United States Patent [19]

Lukic et al.

[11] Patent Number: 5,709,703
[45] Date of Patent: Jan. 20, 1998

[54] STENT DELIVERY DEVICE AND METHOD FOR MANUFACTURING SAME

[75] Inventors: Goran Lukic, Bulach; Marc Gianotti, Wiesendangen, both of Switzerland

[73] Assignee: Schneider (Europe) A.G., Bulach, Switzerland

[21] Appl. No.: 744,036

[22] Filed: Nov. 5, 1996

[30] Foreign Application Priority Data

Nov. 14, 1995 [EP] European Pat. Off. .............. 95117923

[51] Int. Cl.⁶ .................................................. A61B 17/00
[52] U.S. Cl. ......................... 606/198; 623/1; 623/23
[58] Field of Search .................................. 606/108, 191, 606/194, 195, 198, 200; 128/898, 899; 623/1, 12

[56] References Cited

U.S. PATENT DOCUMENTS

| | | |
|---|---|---|
| 3,861,972 | 1/1975 | Glover et al. . |
| 4,553,545 | 11/1985 | Maass et al. . |
| 4,732,152 | 3/1988 | Wallsten et al. . |
| 4,771,773 | 9/1988 | Kropf . |
| 4,848,343 | 7/1989 | Wallsten et al. . |
| 4,875,480 | 10/1989 | Imbert . |
| 4,950,227 | 8/1990 | Savin et al. . |
| 4,990,151 | 2/1991 | Wallsten . |
| 5,026,377 | 6/1991 | Burton et al. . |
| 5,061,275 | 10/1991 | Wallsten et al. . |
| 5,071,407 | 12/1991 | Termin et al. . |
| 5,108,416 | 4/1992 | Ryan et al. . |
| 5,201,757 | 4/1993 | Heyn et al. . |
| 5,405,380 | 4/1995 | Gianotti et al. . |
| 5,464,408 | 11/1995 | Duc . |
| 5,480,423 | 1/1996 | Ravenscroft et al. .............. 623/1 |
| 5,484,444 | 1/1996 | Braunschweiler et al. ......... 623/1 |
| 5,534,007 | 7/1996 | St. Germain et al. ............. 606/198 |
| 5,534,287 | 7/1996 | Lukic . |
| 5,591,172 | 1/1997 | Bachmann et al. . |
| 5,591,226 | 1/1997 | Trerotola et al. . |
| 5,607,466 | 3/1997 | Imbert et al. . |
| 5,628,787 | 5/1997 | Mayer . |
| 5,645,559 | 7/1997 | Hachtman et al. . |
| B1 4,655,771 | 9/1996 | Wallsten . |
| B1 4,954,126 | 5/1996 | Wallsten . |

FOREIGN PATENT DOCUMENTS

| | | |
|---|---|---|
| 0364420A1 | 4/1990 | European Pat. Off. . |
| 0442657A2 | 8/1991 | European Pat. Off. . |
| 0596145A1 | 5/1994 | European Pat. Off. . |
| 0627201A1 | 12/1994 | European Pat. Off. . |
| 90/05554 | 5/1990 | WIPO . |
| 93/17636 | 9/1993 | WIPO . |

*Primary Examiner*—Michael Buiz
*Assistant Examiner*—William W. Lewis
*Attorney, Agent, or Firm*—Peter C. Richardson; Lawrence C. Akers; Philip C. Strassburger

[57] ABSTRACT

The stent delivery device has an elongated sheath with a self-expandable stent placed in contracted condition within the distal area of the sheath. An elongated core is arranged in the sheath for relative longitudinal motion between core and sheath, and drive means are arranged between the core and the stent. Scratch protection tubular means comprise a reinforcement ring secured in the sheath and surrounding the distal end portion of the stent when the stent is in contracted condition in the sheath and a tube of thermoformable material heat shrunk over the proximal end portion of the stent and over the core.

19 Claims, 4 Drawing Sheets

2

STENT DELIVERY DEVICE AND METHOD FOR MANUFACTURING SAME

BACKGROUND OF THE INVENTION

This invention relates to a stent delivery device comprising an elongated sheath having a distal area with a distal end, a self-expandable stent having proximal and distal end portions with proximal and distal ends and a braided tubular wall, said stent being placed in contracted condition within the distal area of the sheath, elongated core means having proximal and distal areas, said core means arranged in said sheath for relative longitudinal motion between the sheath and core means, and drive means between the distal area of the core means and the self-expandable stent, whereby relative longitudinal motion between said sheath and core means results into longitudinal relative motion between said stent and sheath so as to cause radial self-expansion of at least a longitudinal portion of the stent out of the distal area of the sheath or radial contraction of at least a longitudinal portion of the stent into the distal area of the sheath. The invention also relates to a method for manufacturing a stent delivery device.

A stent delivery device is shown in EP 0 596 145 A1, which is incorporated herein in its entirety for all purposes.

Self-expandable stents are currently employed for damaged areas or stenoses of body vessels such as food or air pipes, for support, dilatation, repair or bridging such areas.

Where such stents are for use in blood vessels, the stent delivery device must have, inter alia, a very small radial size in order to be capable to reach narrow and/or tortuous areas of such blood vessels. Furthermore, the requirements for use in blood vessels are extremely tough in terms of integrity of the stent delivery device because particles of the device getting loose and wandering through the blood vessel may cause complications such as thrombosis. On the other hand, self-expandable stents are most commonly those formed of a braiding composed, for example, of a first plurality of parallel stainless steel spring wires helically wound in a first direction crossing a second plurality of parallel stainless steel spring wires helically wound in a second direction opposite to the first one. The braiding is made in a continuous process and the braided material is then cut in lengths each of which will be used to constitute a stent. As the wires composing the braiding are cut, their ends constitute a plurality of sharp edges. Such edges may dangerously scratch and even perforate the sheath upon passage of the stent therethrough for expansion into the body vessel. Such perforations of the sheath may cause particles of the sheath getting loose and wandering into the vessel. In case of a blood vessel, there may be therefore complications such as thrombosis. This scratch and perforation problem is particularly acute at the distal end of the sheath where the stent exits from the sheath to self-expand into the vessel because rubbing at that place is maximal due to the interaction of a very small surface of contact between stent and sheath and of the high radial forces generated by the expanding stent against the sheath. However, this problem of scratching and perforation of the sheath also exists for the proximal end of the stent when the latter rubs along the sheath, and possibly exits from the sheath as is the case for a permanently implanted stent. And the problem repeats at both ends of the stent when the stent is successively partly expanded out of the sheath and retracted into the sheath for precise repositioning purposes in the required area of the vessel. Accordingly, there may be a contradictory requirement between small radial size for the stent delivery device to adequately perform in blood vessels and high strength scratch and perforation resistance for the sheath.

It is an object of the invention to provide a stent delivery device that reduces the aforesaid problems and drawbacks, while allowing a small radial size for the sheath to be performant and safe, particularly for use in blood vessels. It is a further object of the invention to provide a stent delivery device which is economical by the simplicity of its manufacture.

SUMMARY OF THE INVENTION

Accordingly, where the stent delivery device comprises scratch protection tubular means of biocompatible material having an inner wall surrounding at least an end portion of the stent when the latter is in contracted condition in the distal area of the sheath, the risk is reduced of a scratching and/or perforation of the sheath by the distal and/or proximal cutting ends of the stent upon operation thereof through the sheath for self-expansion into a body vessel, and more particularly into a blood vessel where wandering of particles resulting from scratching or perforation of the sheath may be dangerous for the patient. And simultaneously, the sheath may be thin walled as the scratching and perforation resistance is achieved by the scratch protection tubular means. The sheath may be therefore extremely thin, thereby allowing a small radial size for the stent delivery device to efficiently and safely perform through narrow areas such as blood vessels. The scratch protection tubular means do not require complicated or costly structure for the sheath to fully and safely perform anti-scratching and anti-perforation functions. The stent may be repeatedly extracted from and re-inserted into the sheath with a reduced risk for the sheath to release dangerous particles into the blood vessel. And in case of emergency, the doctor may act very rapidly to position the stent even if such a positioning requires repeated extraction of the stent out of the sheath. The doctor may thus concentrate on other major problems without having to slow his action for taking care to avoid potentially trouble causing irregular motions for extracting the stent from the sheath.

The scratch protection tubular means may comprise reinforcement tubular means secured at least in the proximal vicinity of the distal end of the distal area of the sheath. This takes care of the scratch and perforation problem in a critical location of the sheath when rubbing between stent and sheath is particularly important due to the small surface of contact between stent and sheath and high radial forces due to expansion of the stent. The distal end of the sheath is fully protected and may be safely operated through the vessel.

Where the reinforcement tubular means are formed by a reinforcement ring surrounding at least the distal end of the stent when the stent is in contracted condition in the distal area of the sheath, a very simple protection structure is achieved which may be incorporated in and fastened to the sheath at low cost. And when this reinforcement ring has a rectangular cross-section, a relatively long reinforcement surface is obtained in the proximal vicinity of the distal end of the sheath in combination with low radial place consumption.

The reinforcement tubular means may comprise an outer surface embedded in the sheath to achieve simple and efficient assembly of the reinforcement tubular means to the sheath. In a preferred embodiment, the reinforcement tubular means are embedded in a multilayer structure of the sheath to efficiently match the requirements of a safe assembly between sheath and reinforcement tubular means and to simultaneously allow a choice of materials providing a very low friction for the whole stent along the inner wall of the sheath to thereby reduce rubbing in that area and facilitate relative motion between stent and sheath while retaining a low profile for the sheath wall. In a still preferred embodiment, the multilayer structure is heat shrunk on the reinforcement tubular means to intimately mate the tubular means and sheath.

The reinforcement tubular means may be made of metal to offer the strongest resistance to scratching and/or perforation without interfering on the materials used for making the stent. A metallic reinforcement tubular means may also be extremely thin without loosing its resistance to scratching and perforation, which still adds to the profile reduction of the sheath.

In a further embodiment, the reinforcement tubular means are made of a radiopaque metal. In conjunction with a radiopaque marker, for instance conventionally located on the core means at the proximal end of the stent, this radiopaque reinforcement tubular means provide a fixed reference allowing precise knowledge of the percentage of stent which is out of the sheath. Such a percentage knowledge also helps avoiding exaggerated retraction of the stent into the sheath and the resulting potential of damage to the stent or sheath.

In a still further embodiment, the core means extend through the stent and a distal ring of radiopaque material is mounted on the core means within the reinforcement tubular means of radiopaque metal. This allows direct control of the relative position of the stent with respect to the sheath when the stent is retracted into the sheath. Accordingly, it is thereby possible to easily avoid exaggerated retraction of the stent in the sheath and potential damage to the stent or sheath. This may be of great help for the doctor when he has to rapidly withdraw the stent into the sheath for re-positioning purposes.

Within the frame of the aforesaid distal ring of radiopaque material mounted on the core means within the reinforcement tubular means, the device may advantageously comprise tip means ending the distal area of the core means concentrically to the distal ring of radiopaque material and reinforcement tubular means of radiopaque metal. In addition to the usual advantages of a tip configuration for a smooth insertion of the stent delivery system into the body vessel, the coaxial mounting of the tip on the distal ring of radiopaque material and reinforcement tubular means assures a centering of the tip means on the sheath thereby preventing bending or angle making between the tip and sheath and the potential risk of catching and wounding the body vessel in particular in tortuous areas thereof. Hence, the reinforcement tubular means have a positioning or centering function in addition to the anti-scratching, anti-perforation, and control functions. Within this frame, the reinforcement tubular means may have a first outer diameter whereas the tip means have a second outer diameter greater than the first outer diameter. This configuration acts as an extra safety in case of the unexpected (and even highly improbable) escape of the reinforcement tubular means out of the end area of the sheath. In such a case, the larger diameter of the tip means prevents any passage of the reinforcement tubular means distally beyond the tip means and assures recovery of the reinforcement tubular means out of the body vessel.

When the scratch protection tubular means comprise coverage tube means secured to the proximal end portion of the stent and to the core means, a safety is obtained along the distal area of the sheath against the risk of having sheath particles getting loose from the sheath because of rubbing between the proximal end of the stent and the sheath. When combined to the reinforcement tubular means as described hereinbefore, the resulting configuration of the scratch protection tubular means assures full protection of the distal area of the sheath by the maximal reduction of the risk of having particles of the sheath getting loose from the sheath due to the rubbing between stent and sheath.

Where the coverage tube means are formed by a tube of thermoformable material heat shrunk over the proximal end portion of the stent and over the core means, the tube heat shrunk over the proximal end portion of the stent acts as an assembly help for the manufacturing of the stent delivery device. Such an assembly help disposes of using a special tool to very tightly contract the proximal end portion of the stent for inserting the stent into the sheath and avoiding damage to the sheath. And furthermore, the shrunk tube also acts as a protection against kinking of the sheath proximally of the stent because it somewhat fills the room between the proximal end of the stent and the sheath and also reduces continuously the flexibility of the stent at its proximal end portion.

Where the heat shrunk tube comprises longitudinal cuts extending along a distal portion thereof, the heat shrunk tube may easily separate from the proximal end portion of the stent upon expansion thereof out of the sheath, thereby allowing full expansion and release of the stent out of the sheath for permanent implantation thereof.

Within these configurations, a proximal ring of radiopaque material may be mounted on the core means in the immediate proximal vicinity of the proximal end of the stent, said ring of radiopaque material being embedded in the shrunk tube. This arrangement provides for an easy positioning and fastening for a proximal ring of radiopaque material while assuring a smooth transition between the stent and radiopaque ring which also contributes to reduce the kinking potential of the sheath in that area.

According to a method of manufacturing a stent delivery device to incorporate in a simple and efficient way a reinforcement ring as hereinbefore described, there is provided for engaging on a mandrel a reinforcement ring having a proximal end, a distal end, and a first outer diameter, engaging on the mandrel and proximally of the proximal end of the reinforcement ring a first tube of thermoformable material having a second outer diameter greater than said first outer diameter, engaging on the reinforcement ring a second tube of thermoformable material having a third outer diameter substantially equal to said second outer diameter of the first tube of thermoformable material, engaging on the first and second tubes of thermoformable material a third tube of thermoformable material, heat shrinking said third tube of thermoformable material over said first and second tubes of thermoformable material and reinforcement ring, withdrawing the mandrel out of the reinforcement ring and first tube of thermoformable material, and taking off unwanted surplus portions of the heat shrunk material at the distal end of the reinforcement ring.

In sum, the present invention relates to a stent delivery device which has an elongated sheath having a distal area with a distal end; a self-expandable stent having proximal and distal end portions with proximal and distal ends and a braided tubular wall, the stent being placed in a contracted condition within the distal area of the sheath; elongated core means having proximal and distal areas, the core means arranged in the sheath for relative longitudinal motion between the sheath and core means; and drive means between the distal area of the core means and the self-expandable stent, whereby relative longitudinal motion between the sheath and core means results in longitudinal relative motion between the stent and sheath so as to cause radial self-expansion of at least a longitudinal portion of the stent out of the distal area of the sheath or radial contraction of at least a longitudinal portion of the stent into the distal area of the sheath, and scratch protection tubular means of biocompatible material having an inner wall surrounding at least an end portion of the stent when the stent is in contracted condition in the distal area of the sheath. The scratch protection tubular means may have reinforcement tubular means secured at least in the proximal vicinity of the distal end of the distal area of the sheath. The reinforcement tubular means may be formed by a reinforcement ring surrounding at least the distal end portion of the stent when the stent is in a contracted condition in the distal area of the sheath. The reinforcement ring may have a rectangular cross-section. The reinforcement tubular means may have an outer surface embedded in the sheath, optionally embedded in a multilayer structure of the sheath. The multilayer structure may be heat shrunk on the reinforcement tubular means. The reinforcement tubular means may be made of metal, optionally a radiopaque metal. The core means may extend through the stent, and the distal ring of radiopaque material may be mounted on the core means within the reinforcement tubular means of radiopaque metal. The device may have a means ending the distal area of the core means concentrically to the distal ring of radiopaque material and to the reinforcement tubular means of radiopaque metal. The reinforcement tubular means may have a first outer diameter and the tip means may have a second outer diameter greater than the first outer diameter. The scratch protection tubular means may have coverage tube means secured to the proximal end portion of the stent and to the core means. The coverage tube means may be formed by a tube of thermoformable material heat shrunk over the proximal end portion of the stent and over the core means. The heat shrunk tube of thermoformable material may have longitudinal cuts extending along a distal portion thereof. The device may have a proximal ring of radiopaque material mounted on the core means in the immediate proximal vicinity of the proximal end of the stent, the ring of radiopaque material being embedded in the shrunk tube.

The present invention also relates to a stent delivery device comprising (a) an inner member; (b) a radially self-expanding stent disposed about the core, the stent having a distal portion and a proximal portion; (c) a sheath disposed about at least part of the radially self-expanding stent; and (d) a scratch protection element disposed between at least part of the stent and at least part of the sheath. The scratch protection element may be a tube disposed about at least part of the proximal portion of the stent. The scratch protection element may be a metal tube.

The present invention also relates to a method for manufacturing a stent delivery device by (a) engaging on a mandrel a reinforcement ring having a proximal end, a distal end, and a first outer diameter; (b) engaging on the mandrel and proximally of the proximal end of the reinforcement ring a first tube of thermoformable material having a second outer diameter greater than the first outer diameter; (c) engaging on the reinforcement ring a second tube of thermoformable material having a third outer diameter substantially equal to the second outer diameter of the first tube of thermoformable material; (d) engaging on the first and second tubes of thermoformable material a third tube of thermoformable material; (e) heat shrinking the third tube of thermoformable material over the first and second tubes of thermoformable material and reinforcement ring; (f) withdrawing the mandrel out of the reinforcement ring and first tube of thermoformable material; and (g) taking off unwanted surplus portions of the heat shrunk material at the distal end of the reinforcement ring.

BRIEF DESCRIPTION OF THE DRAWINGS

These and other objects, features and advantages of the invention will become readily apparent from the following detailed description with reference to the accompanying drawings which show, diagrammatically and by way of example only, preferred but still illustrative embodiments of the invention.

DETAILED DESCRIPTION OF PREFERRED EMBODIMENTS

Figure 1:
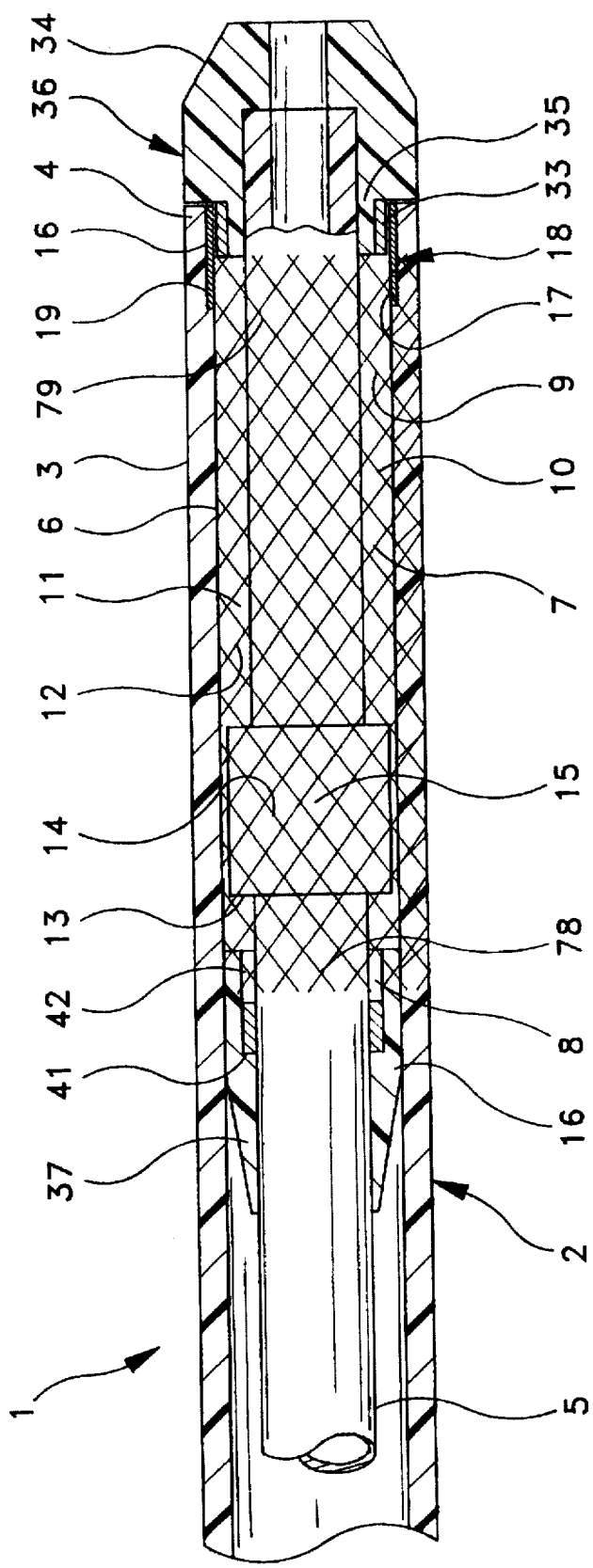
FIG. 1 is a side view partly cut of a device in accordance with the present invention with the stent shown in contracted condition in the sheath.
Figure 2:
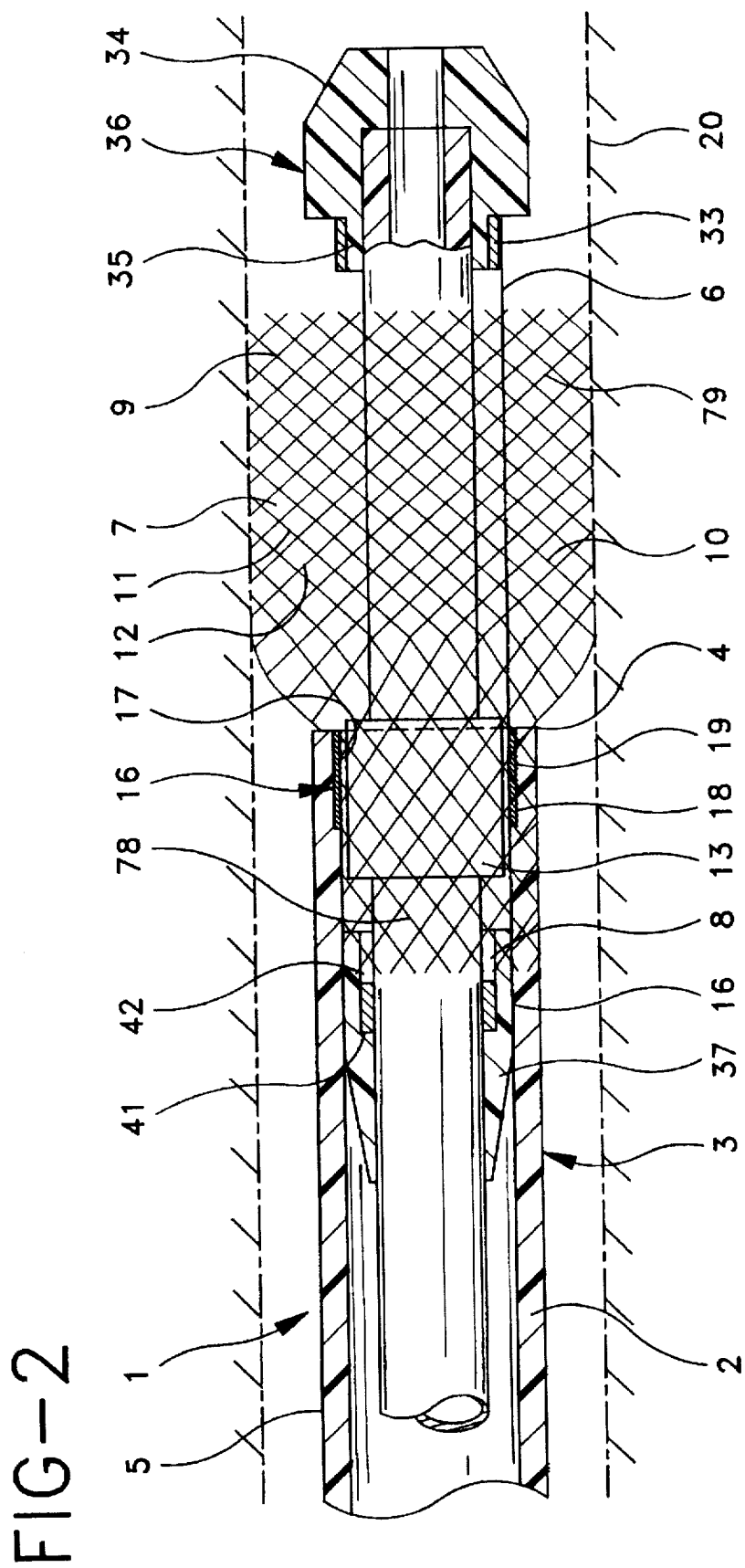
FIG. 2 is a side view similar to that of FIG. 1, however, with the stent shown partly expanded out of the sheath.

The stent delivery device 1 shown in FIGS. 1 and 2 comprises an elongated sheath 2 having a distal area 3 with a distal end 4. The sheath 2 has a proximal area (not shown) adapted to be connected to a conventional T-connector (not shown) for manipulation and contrast fluid supply purposes. Of course, the sheath 2 is made of a biocompatible material.

Within the sheath 2 is arranged an elongated core 5, for example tubular, having a proximal area (not shown) and a distal area 6. The proximal area of the core 5 is adapted to be connected to a conventional luer lock assembly (not shown) for handling purposes. The core 5 is arranged in the sheath 2 for relative longitudinal movement between the sheath and the core. The core is also made of a biocompatible material.

A self-expandable stent 7 having proximal and distal end portions 78 and 79 with a proximal end 8 and a distal end 9 is mounted on the core 7, within the sheath 2 where it is placed in radially contracted condition within the distal area 3 of the sheath 2. The stent 7 has a braided tubular wall 10 which is conventionally composed of a first plurality of parallel stainless steel spring wires 11 helically wound in a first direction crossing a second plurality of parallel stainless steel spring wires 12 helically wound in a second direction opposite to the first one. Such a braided structure allows radial contraction of the stent when it is placed in the sheath 2 as shown in FIG. 1 and radial self-expansion of the stent when it is taken out of the sheath 2 as shown in FIG. 2. This configuration is well known in the art and needs no further description. Of course, other known braidings providing the same effect may be used.

Drive means 13 are provided between the distal area 6 of the core 5 and the self-expandable stent 7. In the example shown, these drive means comprise a pad 14 of soft material which mates with the pits and bosses of the braided tubular wall 10 as depicted at 15 in FIG. 1. Such a configuration and the method for obtaining it are described in EP 0 596 145 A1 which is incorporated herein by reference in its entirety for all purposes. By this arrangement, relative longitudinal motion between the sheath 2 and the core 5 results into longitudinal relative motion between the stent 7 and the sheath 2 so as to cause radial self-expansion of at least a longitudinal portion of the stent 7 out of the distal area 3 of the sheath 2 in a body vessel 20, as shown in FIG. 2, or radial contraction of at least a longitudinal portion of the stent 7 into the distal area 3 of the sheath 2, as shown in FIG. 1.

Scratch protection tubular means 16 of biocompatible material are arranged in the distal area 3 of the sheath 2 so as to have an inner wall 17 surrounding the distal end portion 79 of the stent 7 when the latter is in contracted condition in the distal area 3 of the sheath 2. Such scratch protection tubular means 16 comprise reinforcement tubular means 18 which are secured in the proximal vicinity of the distal end 4 of the distal area 3 of the sheath 2. In the example shown in FIGS. 1 and 2, such reinforcement tubular means 18 are formed by a reinforcement ring which surrounds the distal end portion 79 of the stent 7 when the latter is in contracted condition in the distal area of the sheath 2. Preferably, the ring 18 has a rectangular cross-section and it comprises an outer surface 19 embedded in the sheath 2.

In the embodiment shown in the drawings, the ring 18 is made of metal, preferably a radiopaque metal.

The reinforcement ring 18 may be embedded in a multilayer structure 21 of the sheath 2 and this multilayer structure of the sheath may be heat shrunk on the reinforcement ring 18.

Figure 3:
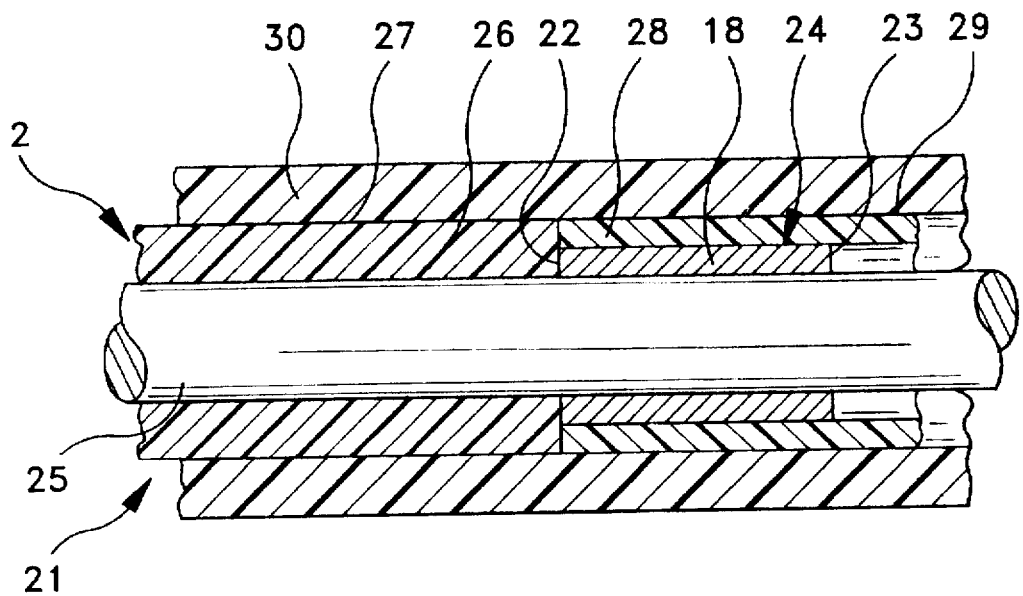
FIGS. 3 and 4 illustrate a method of manufacturing a stent delivery device in accordance with the invention.
Figure 4:
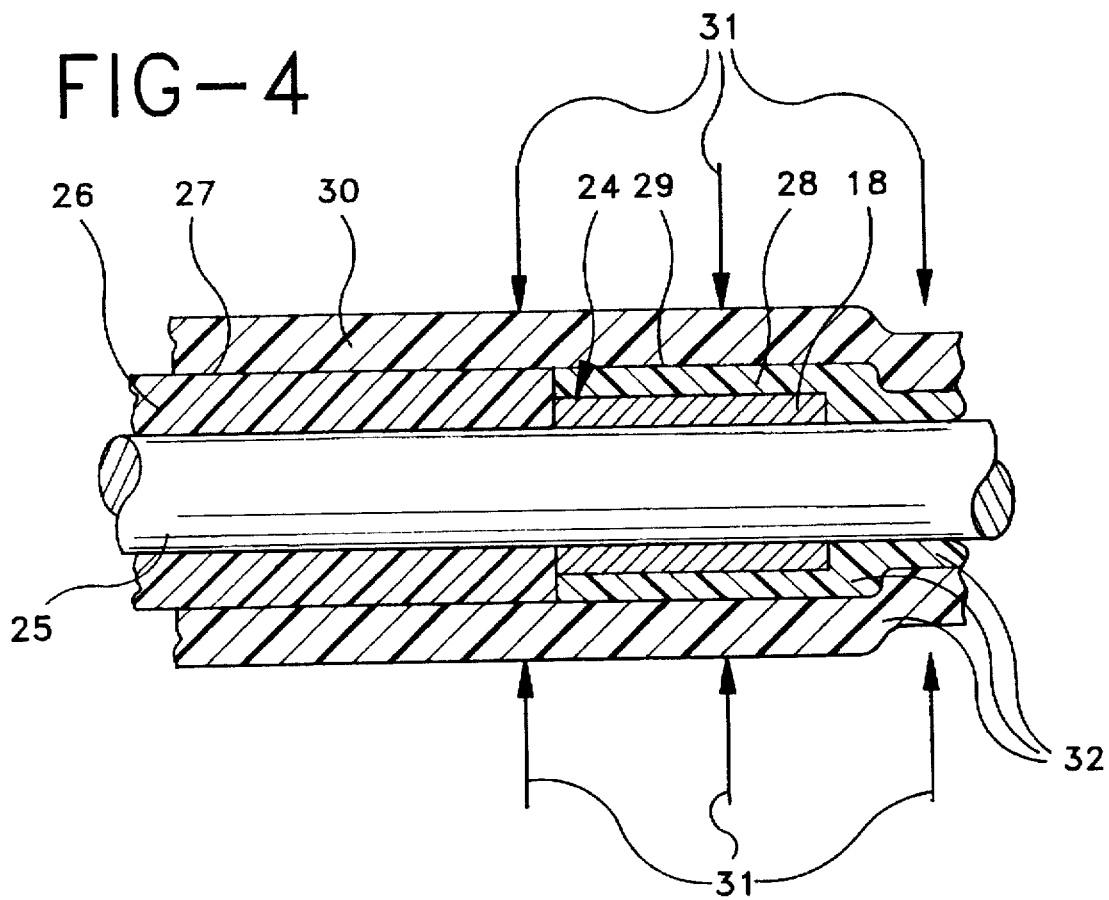

FIGS. 3 and 4 illustrate a method for manufacturing such a configuration. A reinforcement ring 18 having a proximal end 22, a distal end 23, and an outer diameter 24 is engaged on a mandrel 25. A first tube of biocompatible thermoformable material 26 is engaged on the mandrel 25, proximally of the proximal end 22 of ring 18, which first tube has an outer diameter 27 greater than the outer diameter 24 of ring 18. A second tube of biocompatible thermoformable material 28 is engaged on the reinforcement ring 18, which tube has an outer diameter 29 substantially equal to the outer diameter 27 of the first tube 26. The tubes 26 and 28 have thus their outer surfaces substantially aligned. A third tube 30 of thermoformable biocompatible material is engaged on the first and second tubes 26 and 28 and said third tube is heat shrunk over the first and second tubes 26 and 28 and the reinforcement ring 18 as depicted as 31 in FIG. 4. The mandrel 25 is then withdrawn out of the reinforcement ring 18 and first tube 26 and the unwanted surplus portions 32 of the heat shrunk material at the distal end 23 of the reinforcement ring 18 is taken off. By this method, a smooth regular embedding is obtained for the ring in the sheath, avoiding any gaps between the sheath and the ring.

As shown in FIG. 1, the core 5 extends through the stent 7 and a distal ring 33 of radiopaque material is mounted on the core within the reinforcement ring 18. A tip 34 ends the distal area 6 of the core 5 concentrically to the distal ring of radiopaque material 33 and to the reinforcement ring 18 and, to this effect, the tip 34 comprises a proximal tubular shoulder 35 on which is mounted the radiopaque ring 33. The tip 34 has an outer diameter 36 which is greater than the outer diameter 24 of ring 18.

Figure 5:
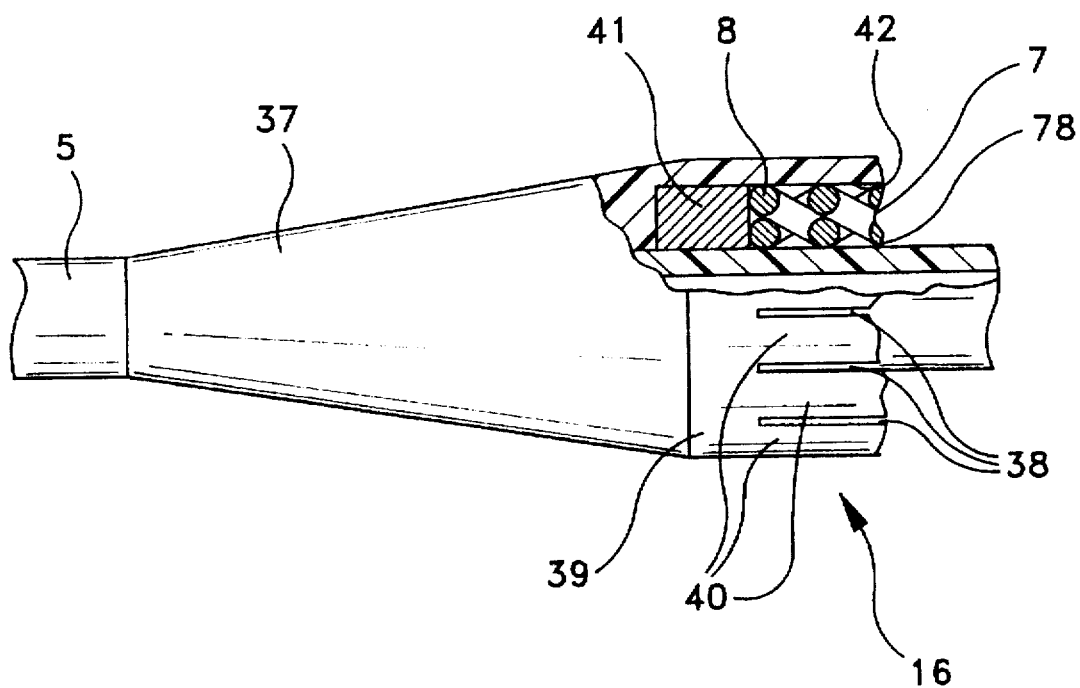
FIG. 5 is a side view partly cut of a detail of FIG. 1.
Figure 6:
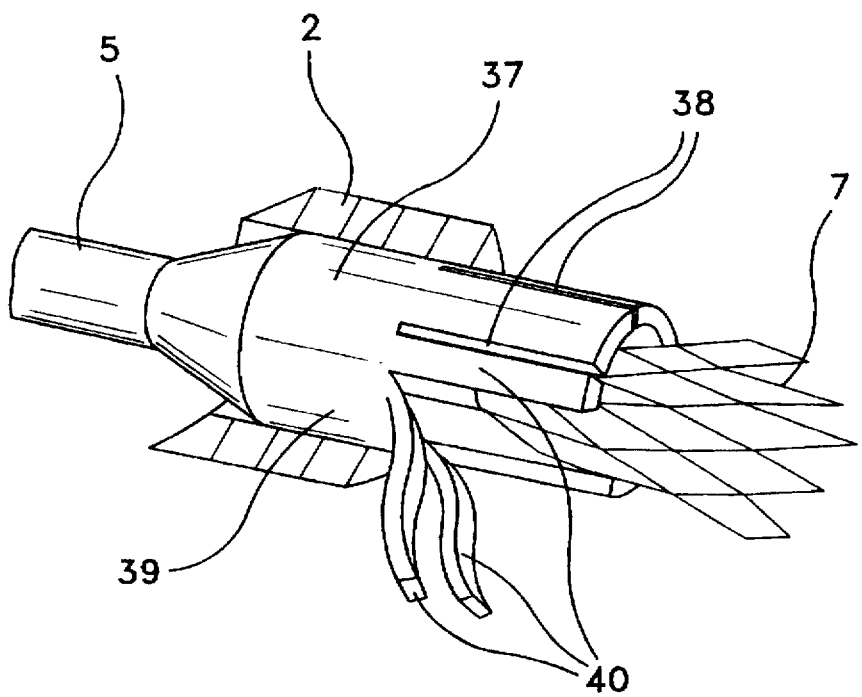
FIG. 6 is a perspective view illustrating the function of the detail of FIG. 5.

As shown in FIGS. 1 and 2 and in more detail in FIGS. 5 and 6 scratch protection tubular means 16 are also arranged in the distal area 3 of the sheath 2 so as to have an inner wall 42 surrounding the proximal end portion 78 of the stent 7 when the latter is in contracted condition in the distal area 3 of the sheath 2. Such scratch protection tubular means 16 comprise coverage tube means 37 secured to the proximal end portion 78 of the stent 7 and to the core 5. In the example shown, such coverage tube means are formed by a tube of thermoformable material heat shrunk over the proximal end portion 78 of the stent 7 and over the core 5. This tube 37 comprises longitudinal cuts 38 extending along a distal portion 39 of the tube 37. These cuts 38 are forming in the tube a plurality of successive tongues 40. As best seen on FIG. 6, these tongues may deploy like flower petals under the radial force exerted by expansion of the stent 7 out of the sheath 2 whereby the tube 37 may easily separate from the proximal end portion of the stent.

A proximal ring 41 of radiopaque material is mounted on the core 5 in the immediate proximal vicinity of the proximal end 8 of the stent 7. This ring 41 of radiopaque material is embedded in the tube 37 which is heat shrunk over the proximal end of the stent and over the core.

Variants are available without departing from the scope of the invention.

For example, the ring 18 may be affixed to the sheath otherwise than by heat shrinking of a structure of the sheath. It may comprise peripheral studs or indentations partly or totally penetrating corresponding recesses provided for in the sheath 2. It may also be affixed to the sheath by means of an appropriate adhesive.

The core 5 may be devoid of a tip such as tip 34.

When the stent is not for permanent implantation in the body vessel, the heat shrunk tube 37 may be replaced by a mere, for instance adhesive, surrounding assembly of the proximal end of the stent to the core.

The drive means 13 may be replaced by any other conventional drive between the core and the stent.

The scratch protection tubular means 16 or ring 18 may extend proximally until the proximal end portion of the stent 7 when the latter is in contracted condition in the distal area 3 of sheath 2. With such an arrangement, the tubular means may also be made of metal, preferably of a radiopaque metal, and assembly thereof to the sheath may be as described for the ring 18. Such a configuration may dispose of using the heat shrunk proximal tube 37 as a sheath protection at the level of the proximal end portion of the stent and as an assembly help for insertion of the stent into the sheath. This extended tubular means may also be secured in the sheath as described for the ring 18.

We claim:

1. A stent delivery device comprising: an elongated sheath having a distal area with a distal end; a self-expandable stent having proximal and distal end portions with proximal and distal ends and a braided tubular wall, said stent being placed in contracted condition within the distal area of the sheath; elongated core means having proximal and distal areas, said core means arranged in said sheath for relative longitudinal motion between the sheath and core means; and drive means between the distal area of the core means and the self-expandable stent, whereby relative longitudinal motion between said sheath and core means results in longitudinal relative motion between said stent and sheath so as to cause radial self-expansion of at least a longitudinal portion of the stent out of the distal area of the sheath or radial contraction of at least a longitudinal portion of the stent into the distal area of the sheath, and scratch protection tubular means of biocompatible material having an inner wall surrounding at least an end portion of the stent when the stent is in contracted condition in the distal area of the sheath.

2. A device according to claim 1, wherein said scratch protection tubular means comprises reinforcement tubular means secured at least in the proximal vicinity of the distal end of the distal area of the sheath.

3. A device according to claim 2, wherein the reinforcement tubular means is formed by a reinforcement ring surrounding at least the distal end portion of the stent when the stent is in a contracted condition in the distal area of the sheath.

4. A device according to claim 3, wherein the reinforcement ring has a rectangular cross-section.

5. A device according to claim 2, wherein the reinforcement tubular means comprises an outer surface embedded in the sheath.

6. A device according to claim 5, wherein the reinforcement tubular means is embedded in a multilayer structure of the sheath.

7. A device according to claim 6, wherein said multilayer structure is heat shrunk on the reinforcement tubular means.

8. A device according to claim 2, wherein the reinforcement tubular means is made of metal.

9. A device according to claim 8, wherein the reinforcement tubular means is made of radiopaque metal.

10. A device according to claim 9, wherein the core means extends through the stent, and wherein a distal ring of radiopaque material is mounted on the core means within the reinforcement tubular means of radiopaque metal.

11. A device according to claim 10, further comprising tip means ending the distal area of the core means concentrically to the distal ring of radiopaque material and to the reinforcement tubular means of radiopaque metal.

12. A device according to claim 11, wherein said reinforcement tubular means has a first outer diameter and the tip means have a second outer diameter greater than said first outer diameter.

13. A device according to claim 1, wherein said scratch protection tubular means comprises coverage tube means secured to the proximal end portion of the stent and to the core means.

14. A device according to claim 13, wherein the coverage tube means is formed by a tube of thermoformable material heat shrunk over the proximal end portion of the stent and over the core means.

15. A device according to claim 14, wherein the heat shrunk tube of thermoformable material comprises longitudinal cuts extending along a distal portion thereof.

16. A device according to claim 14, further comprising a proximal ring of radiopaque material mounted on the core means in the immediate proximal vicinity of the proximal end of the stent, said ring of radiopaque material being embedded in the shrunk tube.

17. A stent delivery device comprising:

(a) an inner member;

(b) a radially self-expanding stent disposed about the inner member, the stent having a proximal portion;

(c) a sheath disposed about at least part of the radially self-expanding stent; and (d) a tubular scratch protection element disposed about at least part of the proximal stent portion and between at least part of the proximal stent portion and at least part of the sheath.

18. The device of claim 17 wherein the scratch protection element comprises a metal tube.

19. A method for manufacturing a stent delivery device comprising:

(a) engaging on a mandrel a reinforcement ring having a proximal end, a distal end, and a first outer diameter;

(b) engaging on the mandrel and proximally of the proximal end of the reinforcement ring a first tube of thermoformable material having a second outer diameter greater than said first outer diameter;

(c) engaging on the reinforcement ring a second tube of thermoformable material having a third outer diameter substantially equal to said second outer diameter of the first tube of thermoformable material;

(d) engaging on the first and second tubes of thermoformable material a third tube of thermoformable material;

(e) heat shrinking said third tube of thermoformable material over said first and second tubes of thermoformable material and reinforcement ring;

(f) withdrawing the mandrel out of the reinforcement ring and first tube of thermoformable material; and (g) taking off unwanted surplus portions of the heat shrunk material at the distal end of the reinforcement ring.

* * * * *